United States Patent
Yamada et al.

(10) Patent No.: US 6,898,961 B2
(45) Date of Patent: May 31, 2005

(54) COMPACT STRUCTURE OF GAS SENSOR AND PRODUCTION METHOD THEREOF

(75) Inventors: Hirokazu Yamada, Nagoya (JP); Takashi Kojima, Kasugai (JP); Isao Watanabe, Nagoya (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 10/155,112

(22) Filed: May 28, 2002

(65) Prior Publication Data

US 2002/0144538 A1 Oct. 10, 2002

Related U.S. Application Data

(62) Division of application No. 09/418,604, filed on Oct. 15, 1999, now Pat. No. 6,415,647.

(30) Foreign Application Priority Data

| Oct. 30, 1998 | (JP) | 10-310664 |
| Apr. 8, 1999 | (JP) | 11-101170 |
| Sep. 6, 1999 | (JP) | 11-251304 |

(51) Int. Cl.[7] .................................. G01N 7/00
(52) U.S. Cl. ............ 73/31.05; 73/23.2; 73/23.31
(58) Field of Search .............. 73/23.31, 23.32, 73/31.05, 23.2; 204/424, 426, 428; 422/98

(56) References Cited

U.S. PATENT DOCUMENTS

| 4,088,555 A | * | 5/1978 | Kita et al. ............ 204/428 |
| 4,141,813 A | * | 2/1979 | Kita et al. ............ 204/428 |
| 4,222,840 A | | 9/1980 | Murphy et al. |
| 4,569,748 A | * | 2/1986 | Yamakawa et al. ...... 204/427 |
| 4,597,849 A | | 7/1986 | Burkhardt et al. |
| 4,717,464 A | | 1/1988 | Oshima et al. |
| 4,733,056 A | * | 3/1988 | Kojima et al. ............ 219/270 |
| 4,818,363 A | | 4/1989 | Bayha et al. |
| 4,883,643 A | | 11/1989 | Nishio et al. |
| 5,098,548 A | * | 3/1992 | Duce ..................... 204/424 |
| 5,139,639 A | | 8/1992 | Holleboom |
| 5,246,562 A | * | 9/1993 | Weyl et al. ............ 204/424 |
| 5,423,972 A | * | 6/1995 | Mann et al. ............ 204/424 |
| 5,573,650 A | | 11/1996 | Fukaya et al. |
| 5,609,825 A | * | 3/1997 | Fukaya et al. ............ 204/421 |
| 5,627,306 A | * | 5/1997 | Yamauchi et al. ......... 204/424 |
| 5,711,863 A | | 1/1998 | Henkelmann et al. |
| 5,762,771 A | | 6/1998 | Yamada et al. |
| 5,785,829 A | * | 7/1998 | Watanabe ............. 204/426 |
| 5,859,361 A | | 1/1999 | Fukaya et al. |
| 5,874,664 A | * | 2/1999 | Watanabe et al. ......... 73/23.32 |
| 6,067,843 A | | 5/2000 | Hafele et al. |
| 6,303,013 B1 | | 10/2001 | Watanabe et al. |

FOREIGN PATENT DOCUMENTS

| DE | 197 03 458 | 7/1997 |
| EP | 0 242 014 | 10/1987 |
| EP | 0 823 631 | 2/1998 |
| EP | 0932039 A2 * | 7/1999 |
| JP | 2-147817 | 6/1990 |
| JP | 8-160002 | 6/1996 |

* cited by examiner

Primary Examiner—Michael Cygan
(74) Attorney, Agent, or Firm—Nixon & Vanderhye PC

(57) ABSTRACT

An improved structure of a gas sensor is provided. The gas sensor includes a hollow housing in which a gas sensing element is disposed, a protective cover installed on an end of the housing, a metallic cover installed on the other end of the housing, and an insulator in which end portions of leads connecting with the gas sensing element are disposed. The insulator is retained at a flange thereof in the housing elastically using a washer. The protective cover is welded at an end thereof to the whole circumference of the end of the housing.

12 Claims, 15 Drawing Sheets

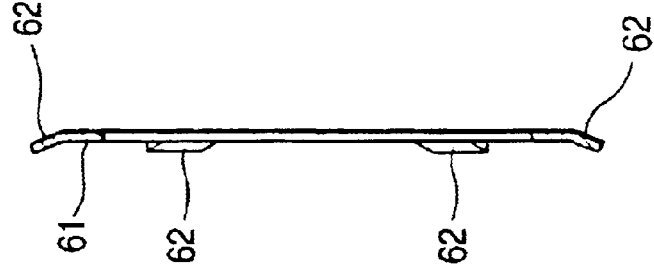
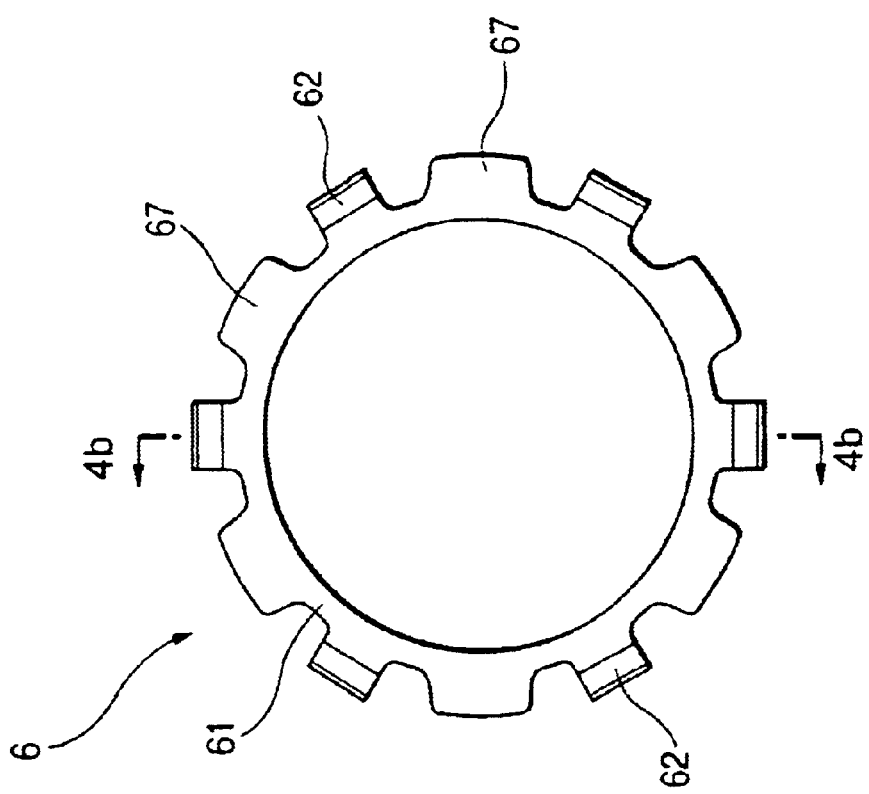

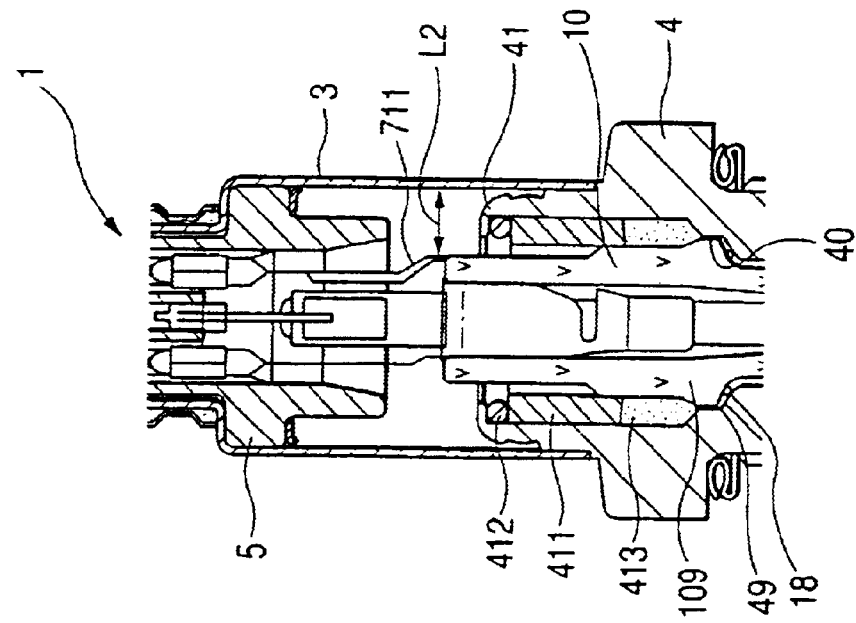

COMPACT STRUCTURE OF GAS SENSOR AND PRODUCTION METHOD THEREOF

This application is a division of application Ser. No. 09/418,604, filed Oct. 15, 1999 now U.S. Pat. No. 6,415,647, the entire contents of which is hereby incorporated by reference in this application.

BACKGROUND OF THE INVENTION

1. Technical Field of the Invention

The present invention relates generally to a gas sensor which may be employed in an air-fuel ratio control system for automotive vehicles for measuring the concentration of gas such as $O_2$, NOx, or CO, and more particularly to an improved compact structure of such a gas sensor and a production method thereof.

2. Background Art

It is known that control of burning of an internal combustion engines as a function of the concentration of oxygen contained in exhaust gasses and the air-fuel ratio of a mixture is effective in the energy saving and the emission control. As one of gas sensors suitable for measuring the concentration of oxygen in exhaust gasses, a gas sensor including a solid electrolyte body made of zirconia is known. This type of gas sensor is, however, required to be reduced in size and production costs and improved in durability and reliability. The approach to satisfaction of these requirements has still left room for improvement.

SUMMARY OF THE INVENTION

It is therefore a principal object of the present invention to provide a gas sensor designed to meet the above discussed requirements in a conventional structure of a gas sensor.

According to one aspect of the invention, there is provided a gas sensor which comprises: (a) a gas sensing element having an gas-exposed portion; (b) a hollow housing having a first and a second end, the housing holding the gas sensing element therein so as to arrange the gas-exposed portion outside the housing for exposure to a gas to be measured; (c) a protective cover installed on the first end of the housing to cover the gas-exposed portion of the gas sensing element; (d) leads connecting with the gas sensing element, extending from the second end of the housing for electrical communication with an external device; (e) a metallic cover installed on the second end of the housing, the metallic cover including a small-diameter portion, a large-diameter portion, and a shoulder portion connecting the smaller-diameter portion and the large-diameter portion; and (f) an insulator including a body and a flange projecting from the body, having disposed therein the leads connecting with the gas sensing element, the body having an outer diameter smaller than an inner diameter of the small-diameter portion of the metallic cover and being disposed within the small-diameter portion, the flange having a first and a second end surface opposed to each other and an outer diameter which is smaller than an inner diameter of the large-diameter portion of the metallic cover and which is greater than the inner diameter of the small-diameter portion, the insulator being disposed in the metallic cover with the first end surface of the flange urged by an elastic member to bring the second end surface into constant engagement with an inner wall of the shoulder portion of the metallic cover.

In the preferred mode of the invention, the metallic cover has a given length. The elastic member is so designed as to produce a first pressure acting on an inner wall of the large-diameter portion of the metallic cover in a radial direction of the large-diameter portion and a second pressure acting on the second end surface of the flange of the insulator in a lengthwise direction of the metallic cover perpendicular to the radial direction of the metallic cover.

The elastic member includes an annular plate and tabs. The annular plate has a diameter smaller than the inner diameter of the large-diameter portion of the metallic cover. The tabs projects from the annular plate so as to establish elastic engagement with the inner wall of the large-diameter portion of the metallic cover.

The elastic member also include guide protrusions each of which is disposed between adjacent two of the tabs and which projects from the annular plate to a circular line smaller than the inner diameter of the large-diameter portion of the metallic cover.

The elastic member may be made of a plate member having opposed surfaces which are symmetrical with each other.

The tabs of the elastic member may be so designed that when the insulator is inserted into the metallic cover, some of the tabs are bent elastically in a first direction away from one of the opposed surfaces of the annular plate by elastic pressure produced by the insertion of the insulator, while the other tabs are bent elastically in a second direction opposite the first direction.

The tabs may extend from the annular plate at an angle of approximately 45° or more to one of the opposed surfaces of the annular plate.

The elastic member may also include a protrusion formed on one of the opposed surfaces thereof.

At least one of the opposed surfaces of the elastic member is painted so that the opposed surfaces have different colors.

The tabs of the elastic member may alternatively be so designed that when the insulator is inserted into the metallic cover, the tabs are bent elastically in the same direction away from one of the opposed surfaces of the annular plate by the elastic pressure produced by the insertion of the insulator.

An elastic insulating member is disposed on an end of the metallic cover remote from the housing to retain the leads therein. If an outer diameter of the elastic insulating member is defined as E, and an outer diameter of the insulator is defined as F, then $E \geq F$.

According to the second aspect of the invention, there is provided a gas sensor which comprises: (a) a gas sensing element having an gas-exposed portion; (b) a hollow housing having a first and a second end, the housing holding the gas sensing element therein so as to arrange the gas-exposed portion outside the housing for exposure to a gas to be measured; (c) a protective cover installed on the first end of the housing to cover the gas-exposed portion of the gas sensing element; (d) leads connecting with the gas sensing element, extending from the second end of the housing for electrical communication with an external device; (e) an insulator retaining therein the leads connecting with the gas sensing element; and (f) a metallic cover joined directly to the housing to hold the insulator therein.

In the preferred mode of the invention, the housing has an outer wall extending between the first and second ends. The metallic cover is welded to the whole of a circumference of the outer wall of the housing.

A welded portion is formed with welding of the metallic cover and the housing which includes a wider portion formed in the metallic cover and a narrower portion formed in the outer wall of the housing. If maximum widths of the wider and narrower portions are defined as A and B, respectively, the depth of the narrower portion is defined as D, and the thickness of the metallic cover 3 defined as T, conditions of B≧0.6A and D≧T are satisfied.

An elastic insulating member is disposed on an end of the metallic cover remote from the housing to retain the leads therein. If an outer diameter of the elastic insulating member is defined as E, and an outer diameter of the insulator is defined as F, then E≧F.

According to the third aspect of the invention, there is provided a gas sensor which comprises: (a) a gas sensing element having an gas-exposed portion; (b) a hollow housing having a first and a second end, the housing holding the gas sensing element therein so as to arrange the gas-exposed portion outside the housing for exposure to a gas to be measured; (c) a protective cover installed on the first end of the housing to cover the gas-exposed portion of the gas sensing element; (d) leads connecting with the gas sensing element, extending from the second end of the housing for electrical communication with an external device; (e) an insulator retaining therein the leads connecting with the gas sensing element; and (f) a metallic cover having a given length, the metallic cover being joined to the housing to hold the insulator therein in engagement of an end of the metallic cover to the housing.

An elastic insulating member is disposed on an end of the metallic cover remote from the housing to retain the leads therein. If an outer diameter of the elastic insulating member is defined as E, and an outer diameter of the insulator is defined as F, then E≧F.

According to the fourth aspect of the invention, there is provided a gas sensor which comprises: (a) a gas sensing element having an gas-exposed portion; (b) a hollow housing having a first and a second end, the housing holding the gas sensing element therein so as to arrange the gas-exposed portion outside the housing for exposure to a gas to be measured; (c) a protective cover installed on the first end of the housing to cover the gas-exposed portion of the gas sensing element; (d) leads connecting with the gas sensing element, extending from the second end of the housing for electrical communication with an external device; (e) an insulator retaining therein the leads connecting with the gas sensing element; and (f) a metallic cover joined to the housing to hold the insulator therein. The hollow housing has an inner chamber and an open end. The open end is crimped to elastically press a metal ring, a sealing member, and an insulating member disposed within the inner chamber to hold the gas sensing element in the inner chamber.

The housing has formed on the inner chamber a step. The gas sensing element has a protrusion which is urged elastically through the metal ring, the sealing member, and the insulating member by crimping the open end of the housing into constant engagement with the step of the housing.

The metal ring is made of a given length of a round bar which is looped.

The gas sensing element is made of a cup-shaped member having formed therein a chamber and has a platinum-made outer electrode formed on the gas-exposed portion and a platinum-made inner electrode formed on an inner wall thereof. A heater is disposed in the chamber of the gas sensing element.

A spring steel-made outer terminal is electrically connected to the outer electrode of the gas sensing element. A spring steel-made inner terminal is electrically connected to the inner electrode. The outer terminal has a conductive extension which is connected to the end portion of one of the leads within the insulator. The inner terminal has a conductive extension which is connected to the end portion of the other of the leads within the insulator and a heater-holding portion which holds the heater in the chamber of the gas sensing element.

The heater is formed with a plate heater which has a rectangular cross section and which is made of a lamination of a substrate formed with a ceramic sheet and a heat generating member.

The housing has an annular groove formed in the first end and an annular skirt extending from the first end around an outer circumference of the annular groove. The protective cover is made of an assembly of an outer cylindrical member and an inner cylindrical member. The outer and inner cylindrical members has flanges which are fitted in the annular groove of the housing. The annular shirt of the housing is crimped inward to elastically press the flanges of the outer and inner cylindrical members together within the annular groove to join the metallic cover to the housing.

An elastic insulating member is disposed on an end of the metallic cover remote from the housing to retain the leads therein. If an outer diameter of the elastic insulating member is defined as E, and an outer diameter of the insulator is defined as F, then E≧F.

According to the fifth aspect of the invention, there is provided a production method of a gas sensor including a gas sensing element having an gas-exposed portion, a hollow housing having a first and a second end portion, holding the gas sensing element therein so as to arrange the gas-exposed portion outside the housing for exposure to a gas to be measured, a protective cover installed on the first end portion of the housing to cover the gas-exposed portion of the gas sensing element, leads connecting with the gas sensing element, extending from the second end portion of the housing for electrical communication with an external device, an insulator retaining therein the leads connecting with the gas sensing element, and a metallic cover joined to the housing to hold the insulator therein. The production method comprises the steps of: (a) preparing an assembly of the housing and the metallic cover attached to an outer wall of the second end portion of the housing; (b) rotating the assembly around a central axis thereof; (c) keeping a rotational speed of the assembly at a given constant value; and (d) emitting a laser beam to a circumference of the metallic cover of the assembly to weld the metallic cover to the housing.

In the preferred mode of the invention, the assembly is rotated with the housing oriented upward and the metallic cover oriented downward.

A difference between an outer diameter of the outer wall of the second end portion of the housing to be welded to the metallic cover and an inner diameter of the metallic cover, that is, the inner diameter of the metallic cover minus the outer diameter of the housing falls within a range of −0.15 mm to 0.1 mm.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 2(*b*) is a sectional view taken along the line 2*b*—2*b* in FIG. 2(*a*);

FIG. 2(*c*) is a sectional view taken along the line 2*c*—2*c* in FIG. 2(*a*);

FIG. 3(*b*) is a longitudinal sectional view which shows installation of an insulator in a cover of a gas sensor of the invention;

FIG. 4(*a*) is a plan view which shows an elastic member used in retaining an insulator;

FIG. 4(*b*) is a sectional view taken along the line 4*b*—4*b* in FIG. 4(*a*);

FIG. 9(*a*) is a partially sectional view which shows installation of a cover on a housing in a prior art structure;

FIG. 9(*b*) is a partially sectional view which shows installation of a cover on a housing in a prior art structure;

FIG. 10(*b*) is a sectional view taken along the line 10*b*—10*b* in FIG. 10(*a*);

FIG. 11(*b*) is a sectional view taken along the line 11*b*—11*b* in FIG. 11(*a*);

FIG. 14(*b*) is a perspective view which shows a terminal leading to an inner electrode of a sensing element;

FIG. 15(*b*) is a partially sectional view which shows arrangement of leads in an upper portion of a cover in a gas sensor of the invention;

FIG. 18(*b*) is a sectional view taken along the line 18*b*—18*b* in FIG. 18(*a*);

FIG. 19(*b*) is a sectional view taken along the line 19*b*—19*b* in FIG. 19(*a*);

FIG. 20(*b*) is a sectional view taken along the line 20*b*—20*b* in FIG. 20(*a*);

FIG. 21(*b*) is a sectional view taken along the line 21*b*—21*b* in FIG. 21(*a*).

DESCRIPTION OF THE PREFERRED EMBODIMENTS

Figure 1:
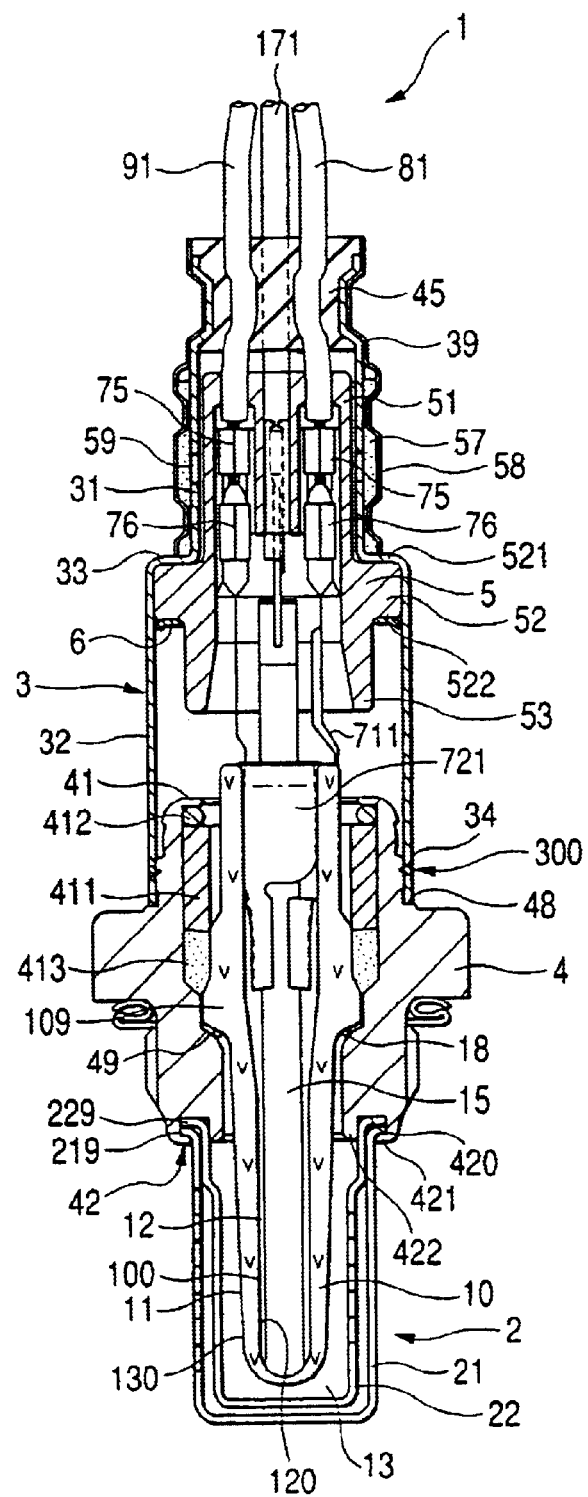
FIG. 1 is a longitudinal sectional view which shows a gas sensor according to the present invention.

Referring now to the drawings, wherein like numbers refer to like parts in several views, particularly to FIG. 1, there is shown a gas sensor 1 according to the present invention which may be employed in automotive air-fuel ratio control systems to measure an oxygen content in exhaust gasses of an internal combustion engine.

The gas sensor 1 generally includes a sensing element 10 and a hollow cylindrical metallic housing 4 having disposed therein the sensing element 10 hermetically. The housing 4 also serves as a sensor mount for mounting the gas sensor 1, for example, in an exhaust pipe of the vehicle. The sensing element 10 has a gas-exposed portion 11 exposed to a gas to be measured in a gas chamber 13 defined by a protective cover assembly 2. The gas sensor 1 also includes leads 81 and 91, an insulator 5, and a metallic cover 3. The leads 81 and 91 connect with the sensing element 10 through connectors 75 and 76. The insulator 5 is retained in the metallic cover 3 and holds therein ends of the leads 81 and 91.

A cover 39 is installed on an upper portion of the metallic cover 3 through a cylindrical water-repellent filter 57 by crimping. The cover 39 and the metallic cover 3 have formed therein first and second air vents 58 and 59 through which the air is introduced into a reference gas chamber 12 defined within the gas sensing element 10 through the water-repellent filter 57.

The insulator 5 consists of a hollow cylindrical body 51 retaining the leads 81 and 91 in an end thereof and a flange 52 greater in diameter than the body 51.

The metallic cover 3 consists of a small-diameter portion 31, a large-diameter portion 32, and a shoulder portion 33 connecting the small-diameter portion 31 and the large-diameter portion 32. The small-diameter portion 31 has the inner diameter which is greater than the outer diameter of the cylindrical body 51 and smaller than the outer diameter of the flange 52. The large-diameter portion 32 has the inner diameter which is greater than the outer diameter of the flange 52. The metallic cover 3 is joined at an end directly to the housing 4.

The insulator 5 is installed in the metallic cover 3 by pressing the surface 522 of the flange 52 through an elastic member 6 fitted into the large-diameter portion 32 to bring the surface 521 of the flange 52 into constant engagement with the shoulder portion 33. Specifically, the insulator 5 is retained by the elastic member 6 and the shoulder 33 of the metallic cover 3.

Figure 2A:
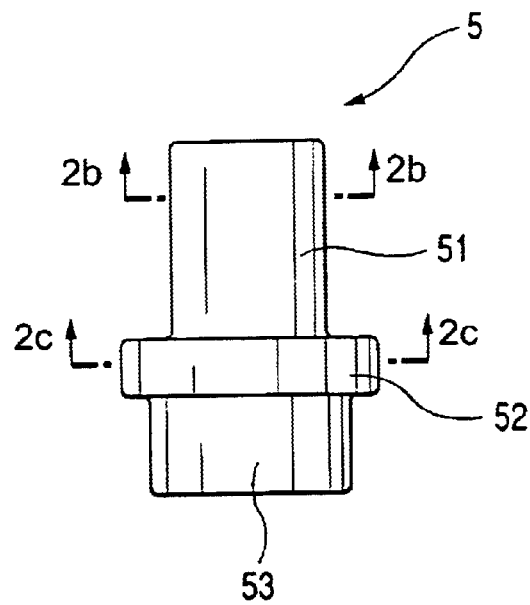
FIG. 2(*a*) is a side view which shows an insulator.
Figure 2B:
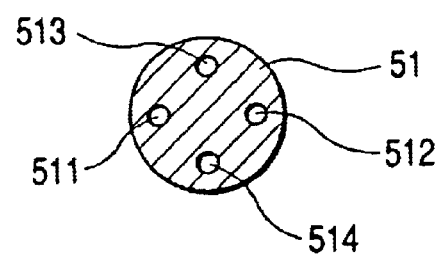
Figure 2C:
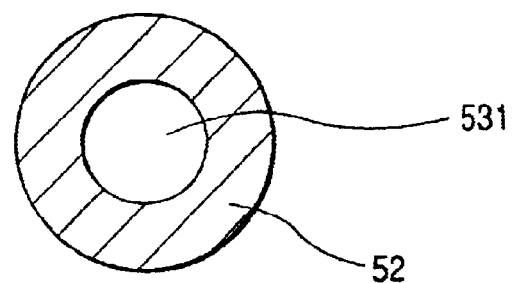

The insulator 5, as clearly shown in FIG. 2(*a*), includes the cylindrical body 51 and the flange 52 greater in diameter than the cylindrical body 51. The insulator 5 also includes a lower cylindrical portion 53 which is slightly greater in diameter than the cylindrical body 51. The cylindrical body 51 has, as shown in FIGS. 1 and 2(*b*), formed therein four holes 511, 512, 513, and 514 through which the leads 81 and 91 connecting with the sensing element 10 and a pair of leads 171 connecting with a heater 15, as will be described later, pass, respectively. The flange 52 and the lower cylindrical portion 53 have, as shown in FIG. 2(c), formed therein a cylindrical bore 531 communicating with the holes 511 to 514.

Figure 3B:
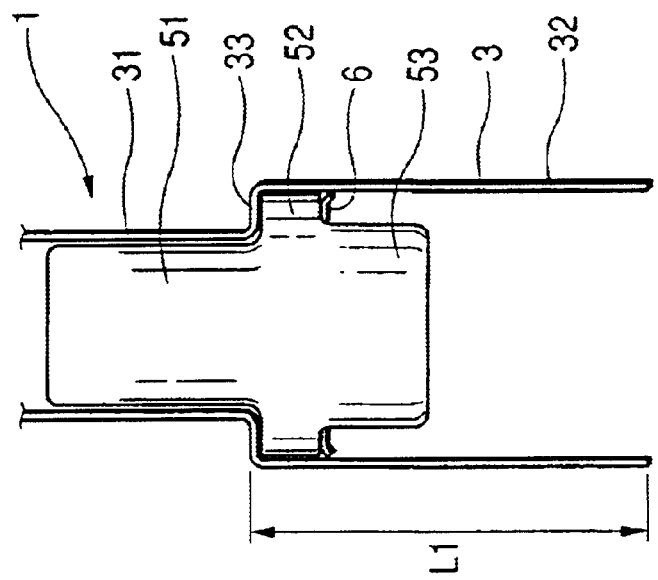
FIG. 3(*a*) is a longitudinal sectional view which shows installation of an insulator in a cover assembly in a prior art structure.

The metallic cover 3, as clearly shown in FIGS. 1 and 3(b), consists of the small-diameter portion 31, the large-diameter portion 32, and the shoulder portion 33. The small-diameter portion 31 has the size sufficient for the cylindrical body 51 of the insulator 5 to be disposed therein. The large-diameter portion 32 has the size sufficient for the flange 52 of the insulator 5 to be disposed therein.

The elastic member 6 is, as clearly shown in FIGS. 4(a) and 4(b), an externally serrated lockwasher which consists of an annular plate 61, six lock tabs 62, and six guide tabs 67. The annular plate 61 is smaller than the inner diameter of the large-diameter portion 32 of the metallic cover 3. The lock tabs 62 project from the outer periphery of the annular plate 61 so as to have the outer diameter greater than the inner diameter of the large-diameter portion 32. Each of the guide tabs 67 is formed between adjacent two of the lock tabs 62 for facilitating the ease of insertion of the elastic member 6 into the metallic cover 3 and increasing the rigidity of the elastic member 6. It is advisable that the number of the lock tabs 62 be greater than or equal to three (3). When the elastic member 6 is installed in the metallic cover 3, it is, as clearly shown in FIG. 1, inserted with the lock tabs 62 all facing toward an opening of the metallic over 3.

The installation of the insulator 5 in the metallic cover 3 is achieved using the elastic member 6 in the following manner.

Figure 5:
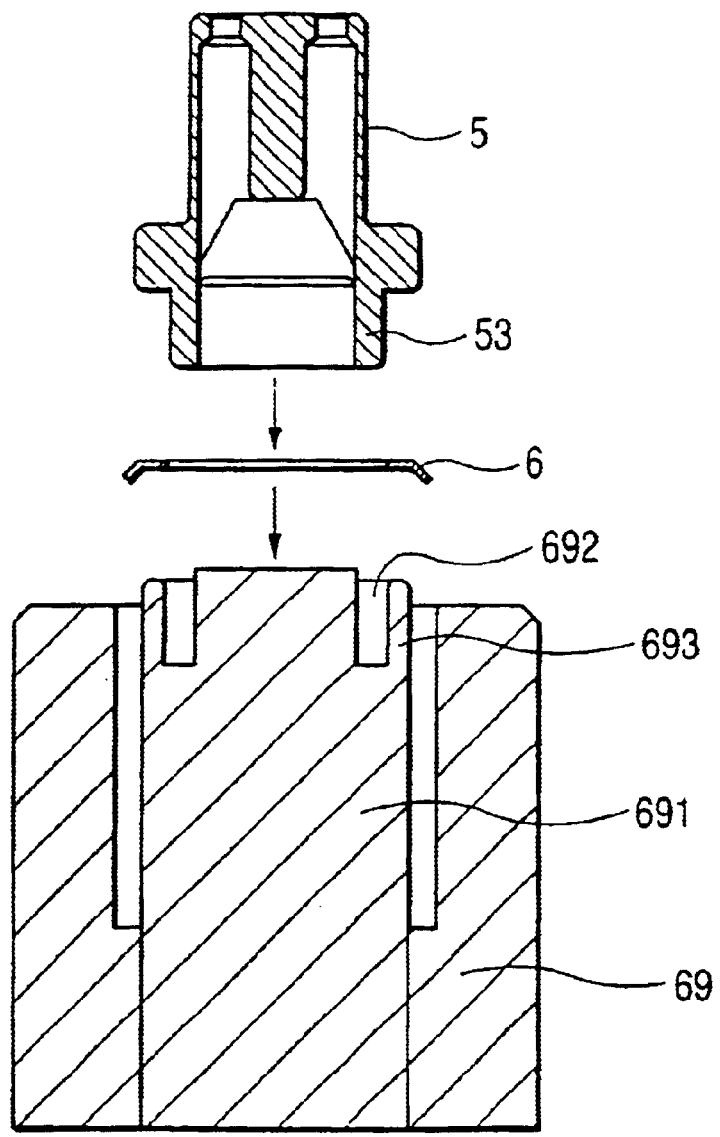
FIGS. 5 and 6 are sectional views which show a sequence of installation processes of installing an insulator in a cover.
Figure 6:
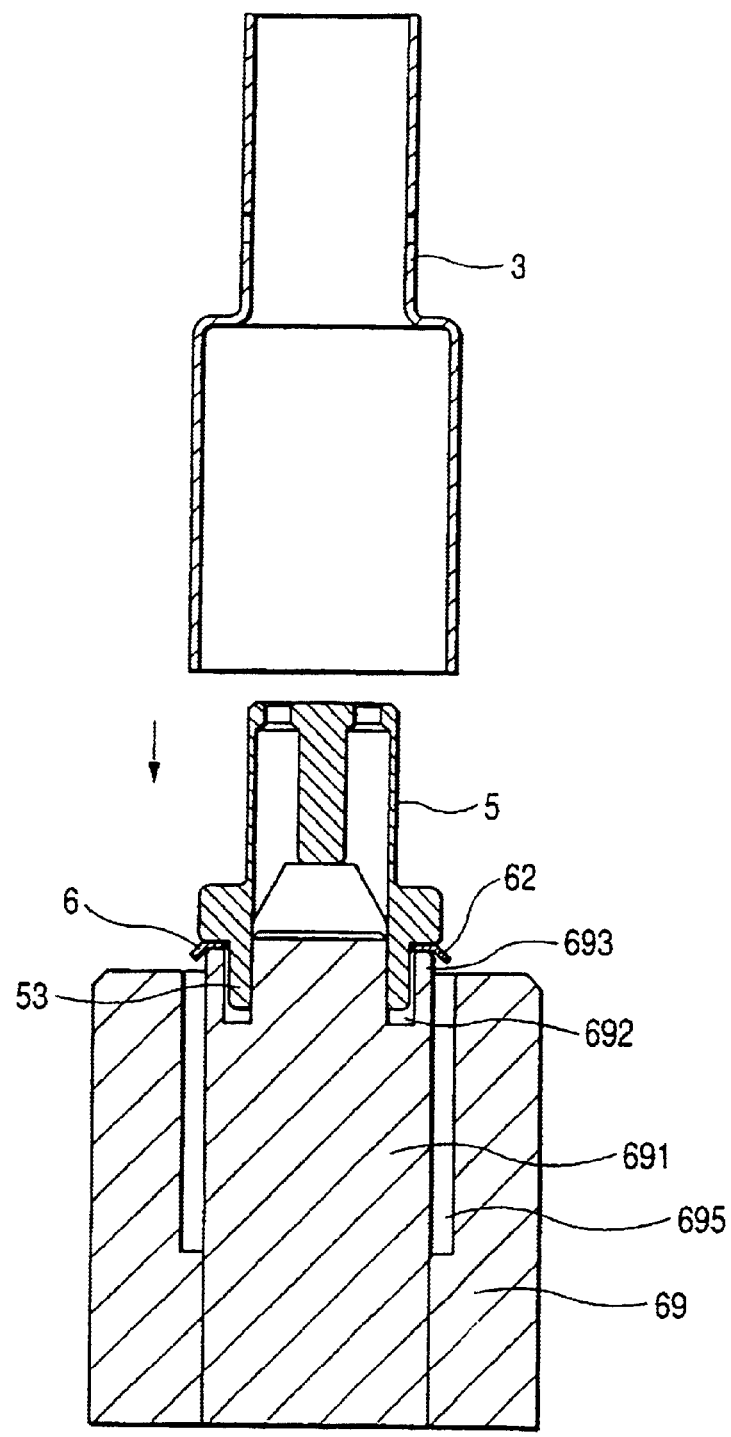
Figure 7:
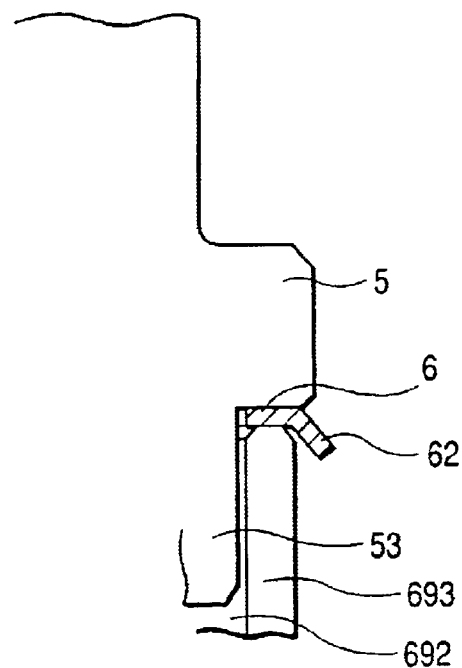
FIG. 7 is a partially enlarged view of FIG. 6.

First, the elastic member 6 and the insulator 5 are, as shown in FIGS. 5 and 6, set on a jig 69. The jig 69 has a central cylinder 691 projecting upward, as viewed in the drawings. The central cylinder 691 has formed in an end thereof an annular groove 692 into which the lower cylindrical portion 53 of the insulator 5 is to be fitted. An outer end wall 693 of the central cylinder 691 defining the annular groove 692 is, as can be seen in FIG. 6, designed to have the width so that an end of the end wall 693 may come into contact only with the annular plate 61 of the elastic member 6 without interfering with the tabs 62 and 67.

Figure 8:
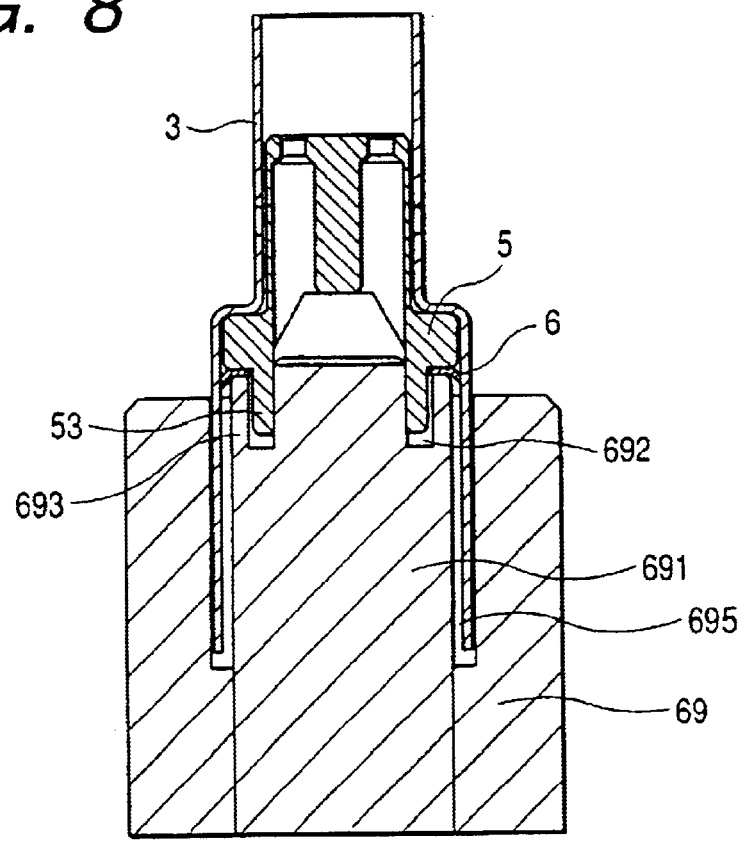
FIG. 8 is a sectional view which shows an insulator installed in a cover in the installation processes shown in FIGS. 5 and 6.

Next, the metallic cover 3 is, as shown in FIGS. 6 and 8, put on the insulator 5 and the elastic member 6 set on the jig 69 and forced, as can be seen in FIG. 8, into a cylindrical chamber 695 defined by the outer wall of the central cylinder 691 within the jig 69, thereby establishing elastic tight engagement of the lock tabs 62 of the elastic member 6 with the inner wall of the metallic cover 3.

The lock tabs 62 of the elastic member 6 are bent at a given obtuse angle away from the surface 521 of the insulator 5. This structure causes the elastic member 6 to be pressed inward when forced into the large-diameter portion 32 of the metallic cover 3, thereby producing the pressure which urges the flange 52 of the insulator 5 into constant engagement with the shoulder 33 of the metallic cover 3.

Figure 3A:
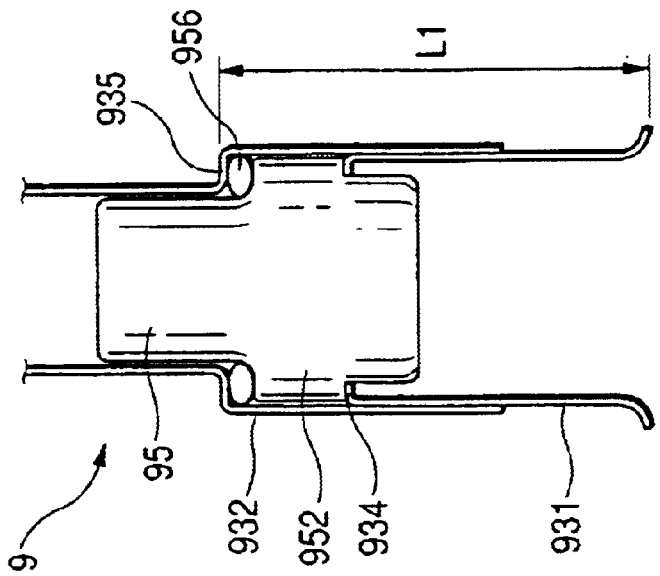

FIG. 3(a) shows, as one example, installation of the insulator 95 in the conventional gas sensor 9. The insulator 95 is substantially identical in structure with the insulator 5 in the embodiment, as described above, and has the flange 952. The insulator 95 is disposed within the outer cover 932. The inner cover 931 is fitted partly within the outer cover 932 with an end 934 urging the flange 952 of the insulator 95 into constant engagement with the shoulder 935 of the outer cover 932 through the spring 956.

Comparison between FIGS. 3(a) and 3(b) shows that the use of the elastic member 6 in the gas sensor 1 of the invention eliminates the need for the inner cover 931 employed in the conventional gas sensor 9 and that the length L1 between the shoulder portion 33 and the lower end of the metallic cover 3 may be determined more accurately than that between the shoulder 935 and the lower end of the inner cover 931.

The elimination of the need for the inner cover 931 allows the inner diameter of the metallic cover 3 to be increased so that the distance L2, as shown in FIG. 9(b), between the metallic cover 3 and the lead 711 of the signal pickup terminal 71 communicating electrically with a measuring electrode, as will be described later in detail, of the sensing element 10 may be increased as compared with that in the conventional gas sensor 9 shown in FIG. 9(a).

The housing 4, as shown in FIGS. 1 and 9(b), has a chamber 40, a crimped end 41, and an annular seat 49. As illustrated in FIG. 1, an outwardly bulging buckled portion is formed when crimped end 41 is formed. The annular seat 49 is formed on an inner wall of the housing 4. The sensing element 10 is retained within the chamber 40 tightly by crimping the end 41 of the housing 4 to press a metallic ring 412, a cylindrical insulator 411, and a seal member 413 downward, as viewed in the drawings, to urge a central flange 109 of the sensing element 10 into constant engagement with the seat 49 through a packing 18.

The conventional gas sensor 9 has, as shown in FIG. 9(a), a housing 94. The housing 94 has an end 940 crimped to press a metallic ring 946 to hold a sensing element 910 within the housing 94 through an insulator 943, a pad 942, and a seal member 941. Between the metallic ring 946 and the insulator 943, a flange 939 of the inner cover 931 is interposed to secure the inner cover 931 on the housing 94. A packing 918 is disposed between the sensing element 910 and an inner wall of the housing 94.

As will be apparent from comparison of the structure of the gas sensor 1 in FIG. 9(b) with that of the conventional gas sensor 9 in FIG. 9(a), the crimped end 41 of the housing 4 is sheathed with the metallic cover 3, thereby resulting in greatly improved corrosion resistance of the end 41.

The conventional gas sensor 9, as discussed above, has the flange 939 of the inner cover 931 retained on the seal member 941, the pad 942, and the insulator 943 within the housing 94. The seal member 941 is made of talc compressed in a production process of the gas sensor 1. Thus, if there is a variation in volume of the seal member 941, it will cause the location of the flange 939 to be changed, which results in a change in volume of a space within which the metallic ring 946 is to be disposed, thus requiring adjustment of the thickness of the metallic ring 946 for crimping the end 940 of the housing 94 completely. The change in location of the flange 939 will also result in a variation in overall length of the gas sensor 9. Compensating for this variation requires adjustment of the spring 956 disposed between the insulator 95 and the outer cover 932. In contrast, the gas sensor 1 of this embodiment has the metallic cover 3 bonded directly to the housing 4. The overall length of the gas sensor 1 is, thus, insensitive to a variation in volume of the seal member 413 made of compressed talc, thereby eliminating the need for adjustment of the thickness or size of any parts.

Figure 10A:
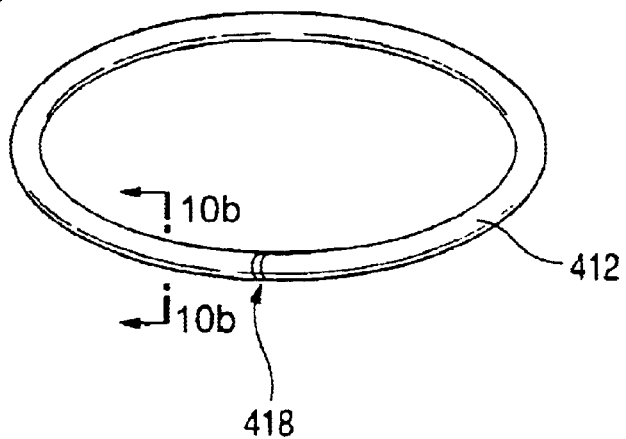
FIG. 10(*a*) is a perspective view which shows a metal ring used in holding a sensing element.
Figure 10B:
Figure 11A:
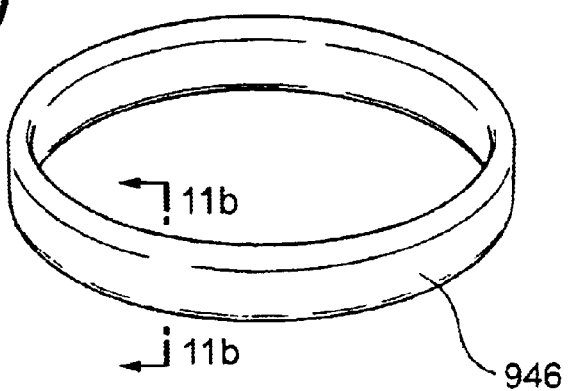
FIG. 11(*a*) is a perspective view which shows a metal ring used in the prior art structure as shown in FIG. 9(*a*)
Figure 11B:

The metallic ring 412 of the gas sensor 1 is, as shown in FIGS. 10(a) and 10(b), made by looping a given length of a round bar and has a gap 418. The metallic ring 941 of the gas sensor 9 is, as shown in FIGS. 11(a) and 11(b), made by machining a jointless round strip member having an oval cross section. This difference in structure allows production costs of the metallic ring 412 to be reduced, resulting in a decreased total costs of the gas sensor 1. The use of the metallic ring 412 is realized with the improvement of airtight sealing established by welding the metallic cover 3 to the whole of a circumference of the housing 4.

Figure 12:
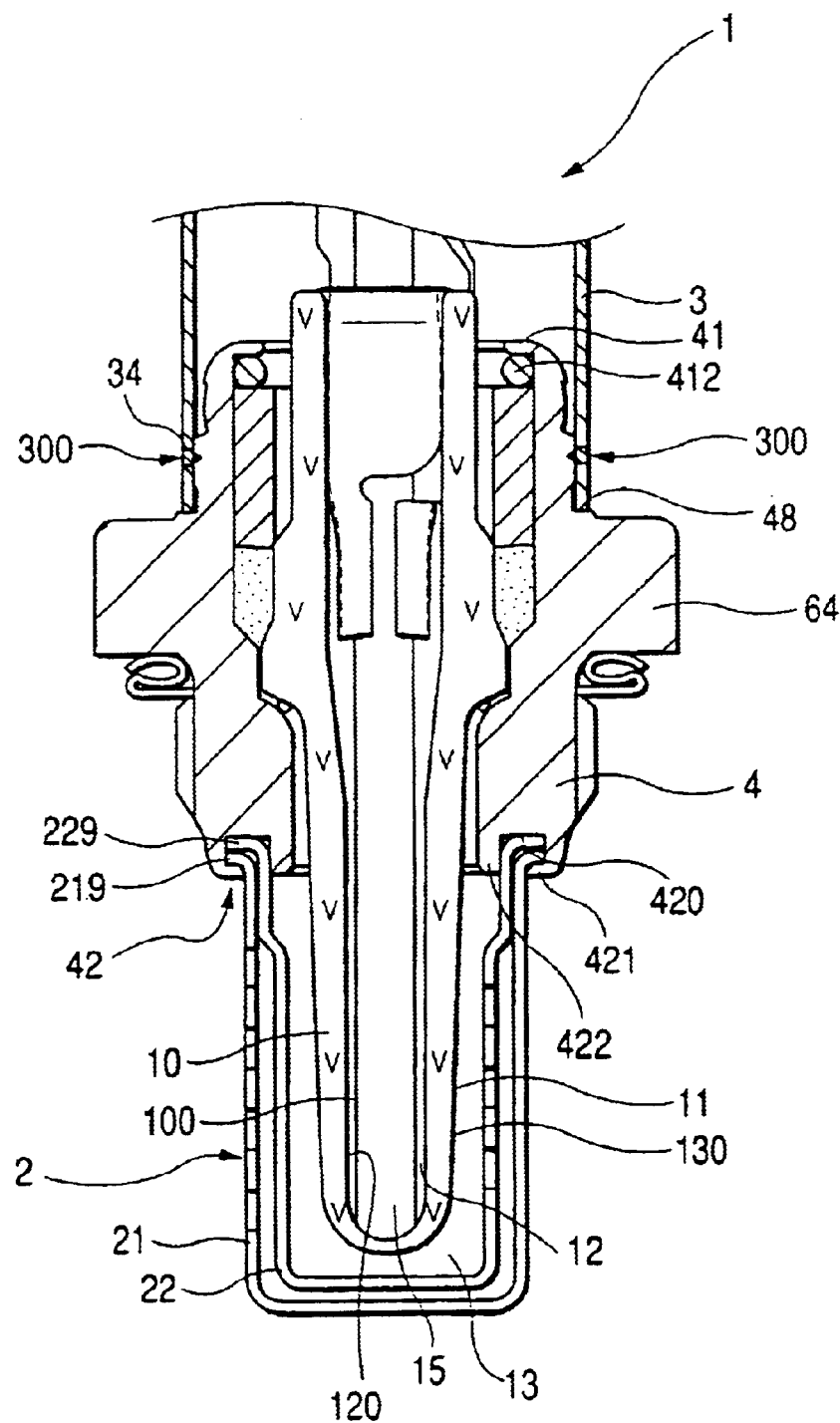
FIG. 12 is a partially sectional view which shows installation of a cover and a cover assembly on a housing.

The protective cover assembly 2 is, as clearly shown in FIG. 12, retained tightly in an annular groove 420 formed in the bottom of the housing 4 by crimping an annular extension or skirt 421 inward. The protective cover assembly 2 consists of outer and inner cylindrical covers 21 and 22 which have ends bent outward to form flanges 219 and 229, respectively The inner cover 22 has an open end bulged so as to be installed in the annular groove 420 in a suitable fit with a guide wall 422. The installation of the protective cover assembly 2 on the housing 4 is achieved by putting the flanges 219 and 229 in the grooves 420 together and bending the skirt 421 inward tightly.

The metallic cover 3 is, as clearly shown in FIGS. 1 and 12, mounted at an end on the housing 4 in constant contact with an annular step 48 formed on a flange 64 and joined at a circumferential portion 300 to the whole of a periphery of a joint portion of an upper portion of the housing 4 by, for example, laser welding. As shown in FIG. 1, the joint portion, to which the metallic cover 3 is welded, is thicker than the bulging, buckled portion formed when crimped end 41 is formed. This structure improves the airtight sealing between the housing 4 and the metallic cover 3 as compared with a conventional structure such as the one shown in FIG. 9(a) in which the inner cover 931 is installed at an end thereof in the housing 94.

The step 48 is machined on an upper surface of the flange 64 to have a flat surface for facilitating establishment of concentricity of the metallic cover 3 and the housing 4 and locating portions of the metallic cover 3 and the housing 4 to be welded to each other accurately.

Figure 13:
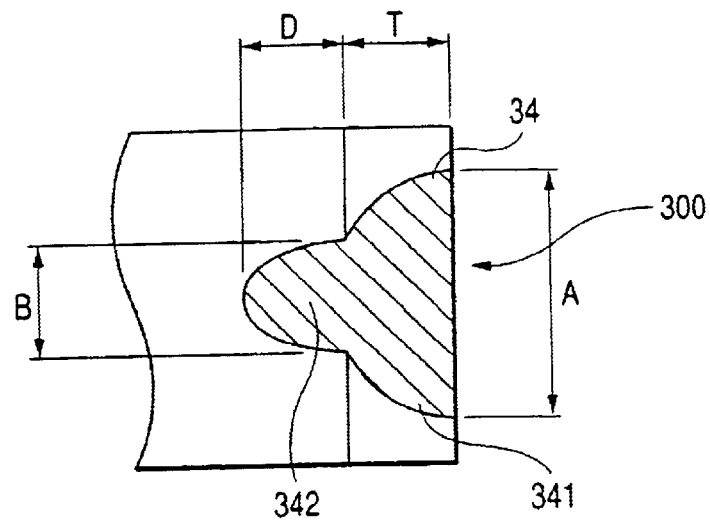
FIG. 13 is a partially sectional view which shows a weld of a housing and a cover.

FIG. 13 shows a cross section of a weld 34 of circumferential portions of the metallic cover 3 and the housing 4 which were fused by the laser welding and then solidified. The weld 34 is, as can be seen from the drawing, made up of a wider half-moon portion 341 formed in the metallic cover 3 and a narrower semi-oval portion 342 formed in the outer wall of the housing 4. If maximum widths of the half-moon portion 341 and the semi-oval portion 342 are defined as A and B, respectively, the depth of the semi-oval portion 342 is defined as D, and the thickness of the metallic cover 3 is defined as T, conditions of $B \geq 0.6A$ and $D \geq T$ are satisfied. In this embodiment, A is 1.0 mm. B is 0.6 mm. D is 0.6 mm. T is 0.6 mm. This results in an improved strength of the joint of the metallic cover 3 and the housing 4.

The sensing element 10 consists of a cup-shaped solid electrolyte body which has formed therein a chamber 100. Within the chamber 100, the heater 15 is disposed for heating the sensing element 10 up to a given operating temperature. The chamber 100 defines a reference gas chamber 12 communicating with the air vents 58 and 59. The sensing element 10 has outer and inner electrodes 130 and 120 both made of Pt. The outer electrode 130 is attached to the gas-exposed portion 11 and functions as a measuring electrode, while the inner electrode 120 is attached to an inner wall of the sensing element 10 and functions as a reference electrode. In operation, the electromotive force is produced between the outer and inner electrodes 130 and 120 as a function of the concentration of a gas within the gas chamber 13 and outputted through the leads 81 and 91.

For the operation of the gas sensor 1 in more detail, reference is made to U.S. appln. Ser. No. 09/196,693, filed on Nov. 20, 1998, assigned to the same assignee as that of this application, disclosure of which is incorporated herein by reference.

Figure 14A:
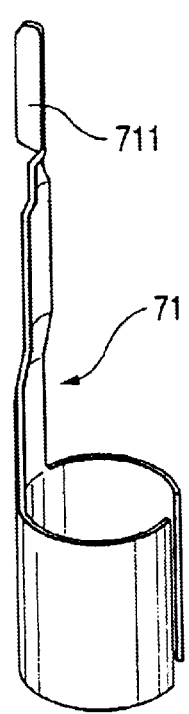
FIG. 14(*a*) is a perspective view which shows a terminal leading to an outer electrode of a sensing element.
Figure 14B:
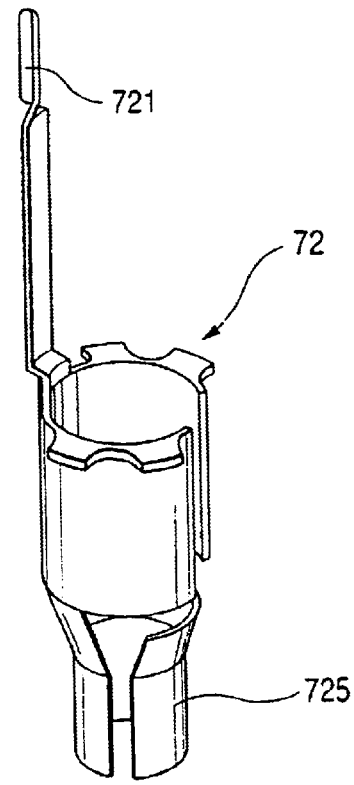

The signal pickup terminal 71, as shown in FIGS. 1 and 14(a), is mounted on the outer wall of the sensing element 10 in electrical connection with the outer electrode 130. The signal pickup terminal 72, as shown in FIGS. 1 and 14(b), is fitted in the chamber 100 of the sensing element 10 in electrical connection with the inner electrode 120 and has a cylindrical holder 725 which holds the heater 15 therein. The signal pickup terminals 71 and 72 have, as already described, the leads 711 and 721 electrically connecting with the leads 81 and 91 through the connectors 75 and 76. The signal pickup terminals 71 and 72 are each made of a heat-resisting spring steel such as INCONEL (trade mark) whose main component is Ni for improving the durability.

Figure 16:
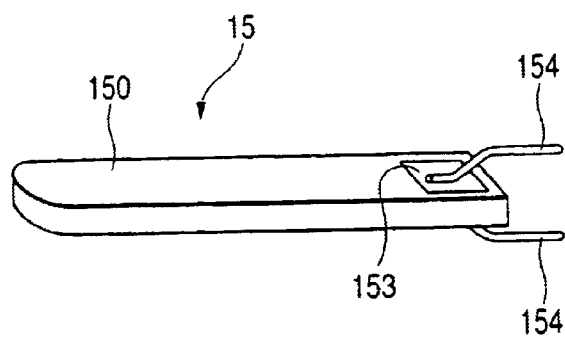
FIG. 16 is a perspective view which shows a heater disposed in a sensing element.

The heater 15, as shown in FIG. 16, includes a ceramic square rod 150 having a rectangular cross section. The ceramic square rod 150 is made of a laminate of substrates each formed with a ceramic sheet and heat generating members. Metallic terminal plates 153 are bonded to opposed surfaces of the ceramic square rod 150 in electrical connection with the heat generating members through the ceramic substrates, respectively. The metallic terminal plates 153 each have formed thereon conductive pins 154 connecting with the leads 171.

Figure 15B:
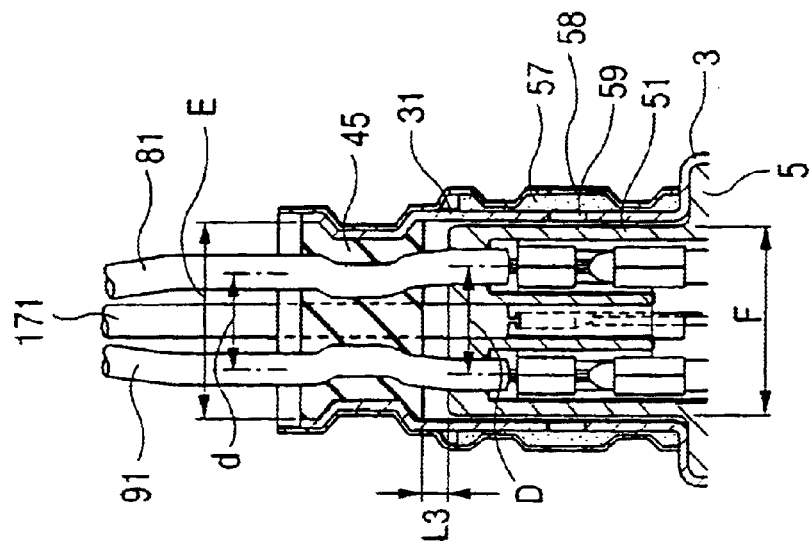
FIG. 15(*a*) is a partially sectional view which shows arrangement of leads in an upper portion of a cover in the prior art structure shown in FIG. 9(*a*)

A rubber bush 45, as clearly shown in FIG. 15(b), is installed in an end of the small-diameter portion 31 of the metallic cover 3. The rubber bush 45 retains therein the leads 81, 91, and 171. The cover 39 is, as described above, installed on the small-diameter portion 31 of the metallic cover 3 by crimping. If the outer diameter of the rubber bush 45 is defined as E, and the outer diameter of the cylindrical body 51 of the insulator 5 is defined as F, then $E \geq F$. In this embodiment, E=10.1 mm. F=9.8 mm. This structure results substantially in agreement of the interval d between opposed two of four holes in the rubber bush 45 through which the leads 81, 91, and 171 pass with the interval D between opposed two of the holes 511 to 514 in the insulator 5.

Figure 15A:
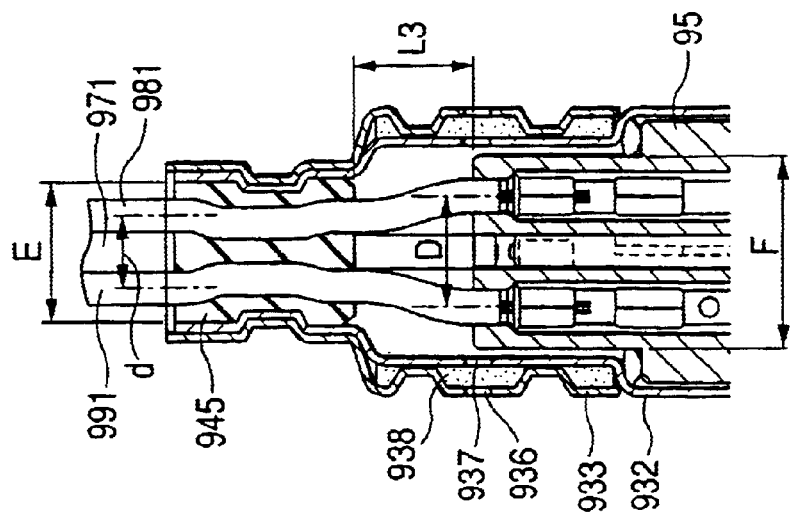

In the conventional gas sensor 9 as shown in FIG. 15(a), the outer diameter E of a rubber bush 945 is smaller than the outer diameter F of the insulator 95. Specifically, E is 6.5 mm, and F is 9.8 mm. This structure results in a difference between the intervals d and D which will require bending the leads 981 and 991 extending from the insulator 95 inward when they are inserted into the rubber bush 945 in an assembling process. It is not advisable that the leads 981 and 991 be bent at sharp angles, thus requiring increase in interval L3 between the insulator 95 and the rubber bush 945 which will result in increase in overall size of the gas sensor 9. In contrast, the structure of the gas sensor 1 shown in FIG. 15(b) allows the interval L3 between the insulator 5 and the rubber bush 45 to be decreased, so that the overall size of the gas sensor 1 can be reduced greatly as compared with the gas sensor 9.

The heater 15 may alternatively be made of a ceramic round bar. The sensing element 10 may alternatively be made of a laminated plate element. For example, U.S. Pat. No. 5,573,650, issued Nov. 12, 1996 to Fukaya et al., teaches such a structure of the sensing element 10, disclosure of which is incorporated herein by reference.

Figure 17:
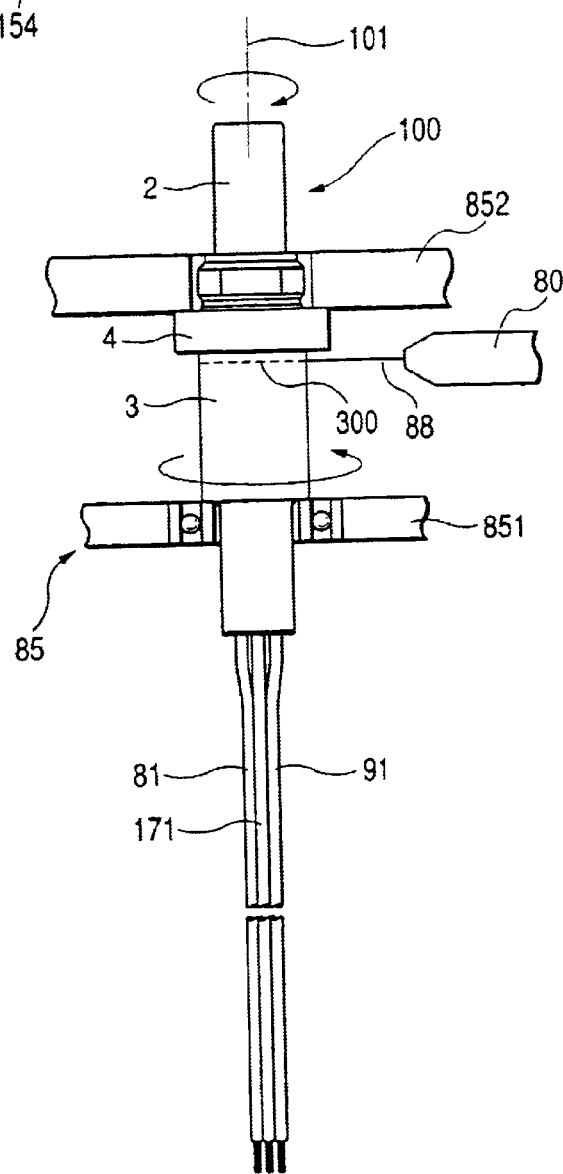
FIG. 17 is an illustration which shows a welding process of joining a cover to a housing.

FIG. 17 shows a process of welding the metallic cover 3 and the housing 4 together according to the second embodiment of the invention.

First, the metallic cover 3 is fitted on the housing 4 to form an assembly 100. Next, the assembly 100 is turned about a longitudinal center line 101 thereof. After a given rotational speed is reached and kept constant, a welding gun 80 is activated to emit a laser beam 88 to the circumferential portion 300 of the metallic cover 3.

Specifically, the outer wall of the housing 4 to be welded to the metallic cover 3 is so machined as to have the diameter greater than the inner diameter of the metallic cover 3 by 0.1 mm. The assembly 100 is formed by pressing the housing 4 into the metallic cover 3.

The difference between the outer diameter of the outer wall of the housing 4 to be welded to the metallic cover 3 and the inner diameter of the metallic cover 3 (i.e., the inner diameter of the metallic cover 3 minus the outer diameter of the housing 4) may be within a range of −0.15 mm to 0.1 mm, preferably within a range of −0.10 mm to 0.05 mm for providing for ease of assembly and hermetic sealing between the metallic cover 3 and the housing 4.

Next, a welding jig 85 is provided which consists of a supporting plate 851 and a rotary plate 852. The metallic cover 3 of the assembly 100 is installed rotatably in the supporting plate 851, while the housing 4 is fixed in the rotary plate 852 so that the metallic cover 3 may be oriented downward, while the housing 4 may be oriented upward.

The rotary plate 852 is rotated using, for example, an electric motor (not shown) to turn the assembly 100. When the circumferential speed of the assembly 100 reaches 1500 mm/minute, it is kept constant. The welding gun 80 is turned on to emit the laser beam 88 to join the metallic cover 3 and the housing 4 together.

The laser beam 88 may be emitted either continuously or intermittently. The circumferential speed of the assembly 100 may be set to another value within a range not sacrificing the welding strength and welded conditions of the metallic cover 3 and the housing 4.

Figure 18A:
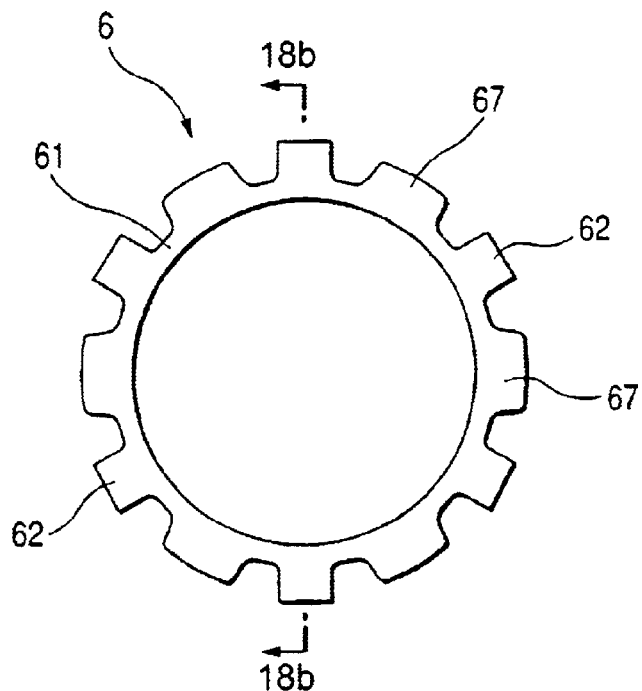
FIG. 18(*a*) is a plan view which shows the first modification of an elastic member used in retaining an insulator.
Figure 18B:
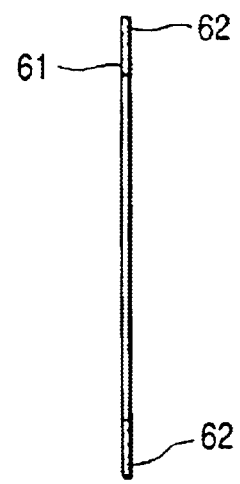

FIGS. 18(a) and 18(b) show a modification of the elastic member 6.

The elastic member 6 is different from the one shown in FIGS. 4(a) and 4(b) only in that the lock tabs 62 and the guide tabs 67 all lie flush with the annular plate 61. In other words, the elastic member 6 has opposed surfaces symmetrical with each other.

Figure 19A:
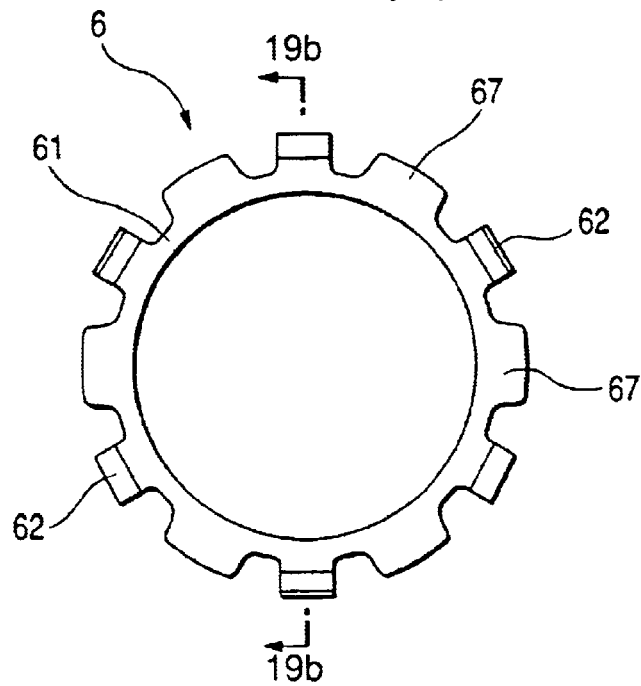
FIG. 19(*a*) is a plan view which shows the second modification of an elastic member used in retaining an insulator.
Figure 19B:
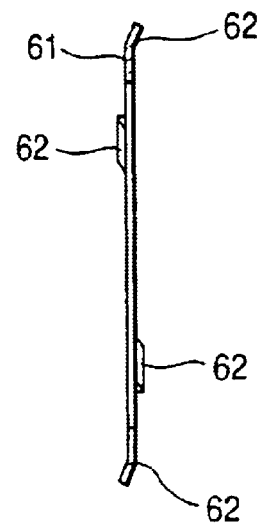

FIGS. 19(a) and 19(b) show the second modification of the elastic member 6.

The elastic member 6 has the lock tabs 62 bent alternately in opposite directions. In this modification, opposed surfaces of the elastic member 6 are, like the above first modification, symmetrical with each other, which will allow a workman to place the elastic member 6 on the jig 69, as shown in FIG. 6, in installation of the insulator 5 in the metallic cover 3 without having to pay attention to orientation of the elastic member 6.

Figure 20A:
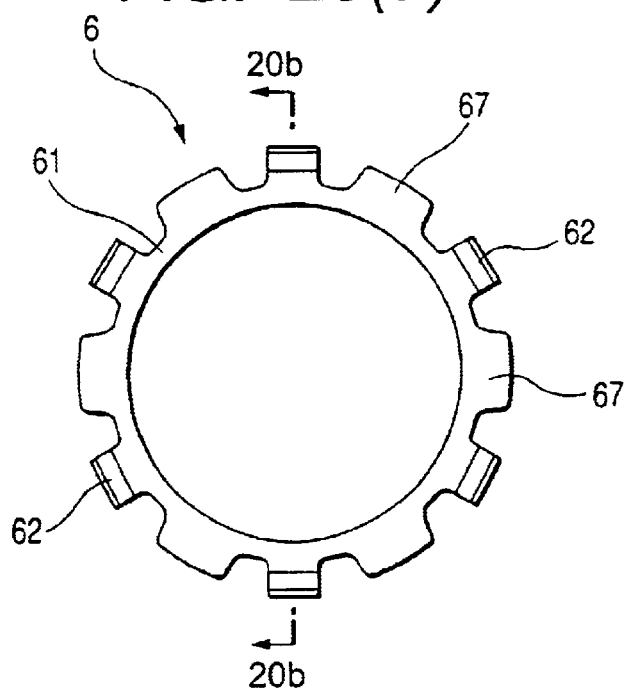
FIG. 20(*a*) is a plan view which shows the third modification of an elastic member used in retaining an insulator.
Figure 20B:
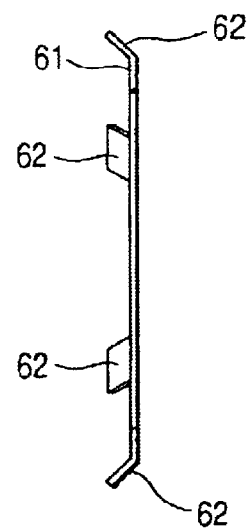

FIGS. 20(a) and 20(b) show the third modification of the elastic member 6 which is different from the one shown in FIGS. 4(a) and 4(b) only in that the lock tabs 62 are all bent in the same direction at an angle of 45° or more to the surface of the annular plate 61.

Figure 21A:
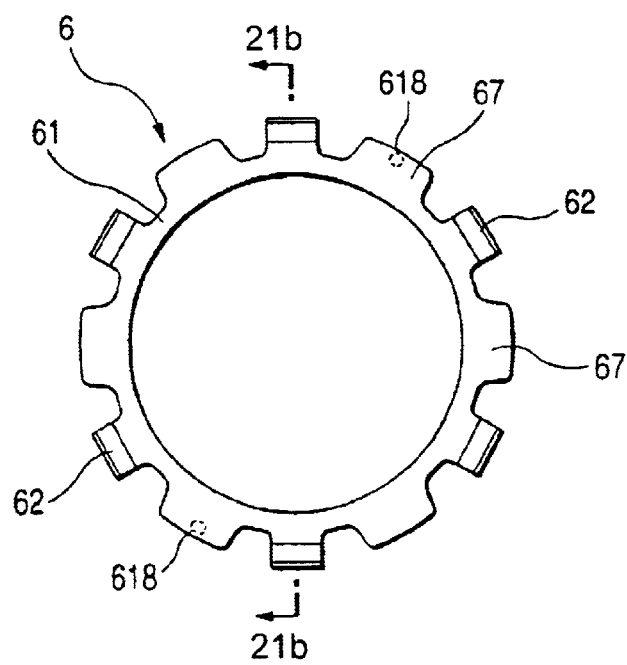
FIG. 21(*a*) is a plan view which shows the fourth modification of an elastic member used in retaining an insulator.
Figure 21B:
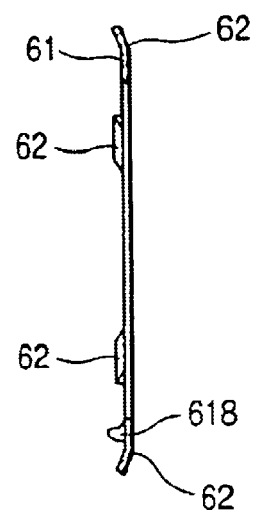

FIGS. 21(a) and 21(b) show the fourth modification of the elastic member 6 which is different from the one shown in FIGS. 4(a) and 4(b) only in that two protrusion 618 are formed on the diametrically opposed guide tabs 67 as a mark which a workman uses in determining which surface of the elastic member 6 is to be oriented to the inside of the metallic cover 3 when installing the insulator 5 in the metallic cover 3.

Specifically, the protrusions 618 extend in the same direction as that in which the lock tabs 62 are bent so as not to interfere with the insulator 5 when installed in the metallic cover 3. The number of the protrusions 618 is not limited to two (2), and at least one protrusion 618 may be provided on the elastic member 6. In either of the third and fourth modifications, it becomes easy for a workman to visually perceive one of opposed surfaces of the elastic member 6 to be oriented toward the inside of the metallic cover 3 in installation of the insulator 5. To this end, it is also advisable that either of the opposed surfaces of the elastic member 6 be colored or that the opposed surfaces be painted in different colors.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas sensor comprising:

a gas sensing element having a gas-exposed portion;

a hollow housing made of a one-piece member which has a first and a second end and an outer wall extending between said first and second ends, said housing holding said gas sensing element therein so as to arrange the gas-exposed portion outside the housing for exposure to a gas to be measured;

a protective cover installed on the first end of said housing to cover the gas-exposed portion of said gas sensing element;

leads connecting with said gas sensing element, extending from the second end of said housing for electrical communication with an external device;

an insulator retaining therein said leads connecting with said gas sensing element; and a metallic cover in which said insulator is held, wherein said hollow housing has an inner chamber and wherein the second end of said hollow housing comprises an open end, a buckled portion, and a joint portion, the open end being crimped inwardly of said hollow housing to elastically press a metal ring, a sealing member, and an insulating member disposed within the inner chamber to hold said gas sensing element in the inner chamber, the buckled portion resulting from inward crimping of the open end, being closer to the first end of said hollow housing than the open end, and bulging outwardly of said housing, the joint portion being closer to the first end of said hollow housing than the buckled portion and greater in wall thickness than the buckled portion, and wherein said metallic cover has an end portion fitted on the outer wall of said housing, a circumferential portion of the fitted end portion of said metallic cover being welded to the whole of a circumference of the joint portion of said housing so as to dispose the inwardly crimped open end, the buckled portion, and the joint portion of said housing inside said metallic cover.

2. A gas sensor as set forth in claim 1, wherein said housing has formed on the inner chamber a step, and wherein said gas sensing element has a protrusion which is urged elastically through the metal ring, the sealing member, and the insulating member by crimping the open end of said housing into constant engagement with the step of said housing.

3. A gas sensor as set forth in claim 1, wherein the metal ring is made of a given length of a round bar which is looped.

4. A gas sensor as set forth in claim 1, wherein said gas sensing element is made of a cup-shaped member having formed therein a chamber and has a platinum-made outer electrode formed on the gas-exposed portion and a platinum-made inner electrode formed on an inner wall thereof, and further comprising a heater disposed in the chamber of said gas sensing element.

5. A gas sensor as set forth in claim 4, comprising a spring steel-made outer terminal electrically connected to the outer electrode of said gas sensing element and a spring steel-made inner terminal electrically connected to the inner electrode, the outer terminal having a conductive extension which is connected to the end portion of one of said leads within said insulator, the inner terminal having a conductive extension which is connected to the end portion of the other of said leads within said insulator and a heater-holding portion which holds said heater in the chamber of said gas sensing element.

6. A gas sensor as set forth in claim 4, wherein said heater is formed with a plate heater which has a rectangular cross section and which is made of a lamination of a substrate formed with a ceramic sheet and a heat generating member.

7. A gas sensor as set forth in claim 1, wherein said housing has an annular groove formed in the first end and an annular skirt extending from the first end around an outer circumference of the annular groove, and wherein said protective cover is made of an assembly of an outer cylindrical member and an inner cylindrical member, the outer and inner cylindrical members having flanges which are fitted in the annular groove of said housing, the annular skirt of said housing being crimped inward to elastically press the flanges of the outer and inner cylindrical members together within the annular groove to join said metallic cover to said housing.

8. A gas sensor as set forth in claim 1, further comprising an elastic insulating member disposed on an end of said metallic cover remote from said housing to retain said leads therein, and wherein if an outer diameter of the elastic insulating member is defined as B, and an outer diameter of said insulator is defined as F, then $B \geq F$.

9. A gas sensor as in claim 1, wherein said hollow housing further comprises a radial flange having a flat upper surface for engaging an end edge of said end portion of said metallic cover.

10. A gas sensor as in claim 1, wherein a welded portion is formed by said welding of said metallic cover and said housing, said welded portion including a wider portion formed in aid metallic cover and a narrower portion formed in the outer wall of said housing.

11. A gas sensor as in claim 10, wherein if maximum widths of the wider and narrow portions are defined as A and B, respectively, the depth of the narrower portion is defined as D, and the thickness of said metallic cover is defined as T, the following conditions are satisfied: $B \geq 0.6A$ and $D \geq T$.

12. A gas sensor as set forth in claim 1, wherein the open end of said hollow housing is bent inwardly by crimping and covered with said metallic cover.

* * * * *